United States Patent
Hochrein et al.

(12)

(10) Patent No.: US 12,133,944 B2
(45) Date of Patent: Nov. 5, 2024

(54) APPARATUS AND METHOD FOR DETERMINING THE STATIC PATIENT PRESSURE

(71) Applicant: Fresenius Medical Care Deutschland GmbH, Bad Homburg (DE)

(72) Inventors: Torsten Hochrein, Hausen (DE); Frank Hedmann, Volkach (DE)

(73) Assignee: FRESENIUS MEDICAL CARE DEUTSHLAND GMBH, Bad Homburg (DE)

( * ) Notice: Subject to any disclaimer, the term of this patent is extended or adjusted under 35 U.S.C. 154(b) by 1084 days.

(21) Appl. No.: 16/966,169

(22) PCT Filed: Jan. 24, 2019

(86) PCT No.: PCT/EP2019/051798
§ 371 (c)(1),
(2) Date: Jul. 30, 2020

(87) PCT Pub. No.: WO2019/149620
PCT Pub. Date: Aug. 8, 2019

(65) Prior Publication Data
US 2021/0038797 A1    Feb. 11, 2021

(30) Foreign Application Priority Data
Jan. 31, 2018 (DE) ...................... 10 2018 102 151.8

(51) Int. Cl.
*A61M 1/28*     (2006.01)
*A61M 1/14*     (2006.01)

(52) U.S. Cl.
CPC ............ *A61M 1/281* (2014.02); *A61M 1/154* (2022.05); *A61M 1/155* (2022.05);
(Continued)

(58) Field of Classification Search
CPC ...... A61M 1/154; A61M 1/155; A61M 1/159; A61M 1/281; A61M 1/282;
(Continued)

(56) References Cited

U.S. PATENT DOCUMENTS

| 2012/0310148 A1 | 12/2012 | Hedmann et al. |
| 2015/0057601 A1 | 2/2015 | Ly et al. |

(Continued)

FOREIGN PATENT DOCUMENTS

| DE | 4431126 | 12/1995 |
| EP | 2776085 | 9/2014 |

(Continued)

*Primary Examiner* — Kami A Bosworth
(74) *Attorney, Agent, or Firm* — Jacobson Holman PLLC

(57) ABSTRACT

The present invention relates to an apparatus for determining the static patient pressure, wherein the apparatus comprises a pump in communication with a patient line for conveying a dialysis solution into the abdomen of the patient, and blocking means, in particular a valve by which the patient line is blockable, wherein the apparatus has a pressure chamber that is in fluid communication with the patient line with an open blocking element, with a pressure measurement device furthermore being provided that is arranged such that it measures the pressure in the pressure chamber or a pressure correlated with it; and wherein the apparatus comprises a control unit that is configured such that it effects a pressure build-up in the pressure chamber to a measurement pressure in a first step and opens the blocking element in a second step so that the patient line or a part section thereof is acted on by the measurement pressure of the pressure chamber and with the apparatus having an evaluation unit that evaluates the measured pressure after the opening of the blocking element.

8 Claims, 1 Drawing Sheet

(52) U.S. Cl.
CPC .......... *A61M 1/1565* (2022.05); *A61M 1/159* (2022.05); *A61M 2205/12* (2013.01); *A61M 2205/18* (2013.01); *A61M 2205/3344* (2013.01); *A61M 2210/1021* (2013.01)

(58) Field of Classification Search
CPC ...... A61M 2205/12; A61M 2205/3344; A61M 1/28; A61M 1/284; A61M 2005/16863; A61M 2005/16868; A61M 2005/16872
See application file for complete search history.

(56) References Cited

U.S. PATENT DOCUMENTS

2017/0296731 A1* 10/2017 Crawford .............. A61M 1/154
2017/0342972 A1    11/2017 Wilt et al.
2018/0001009 A1     1/2018 Crawford et al.

FOREIGN PATENT DOCUMENTS

WO   WO2106/080883    5/2016
WO   WO2016/193930   12/2016

* cited by examiner

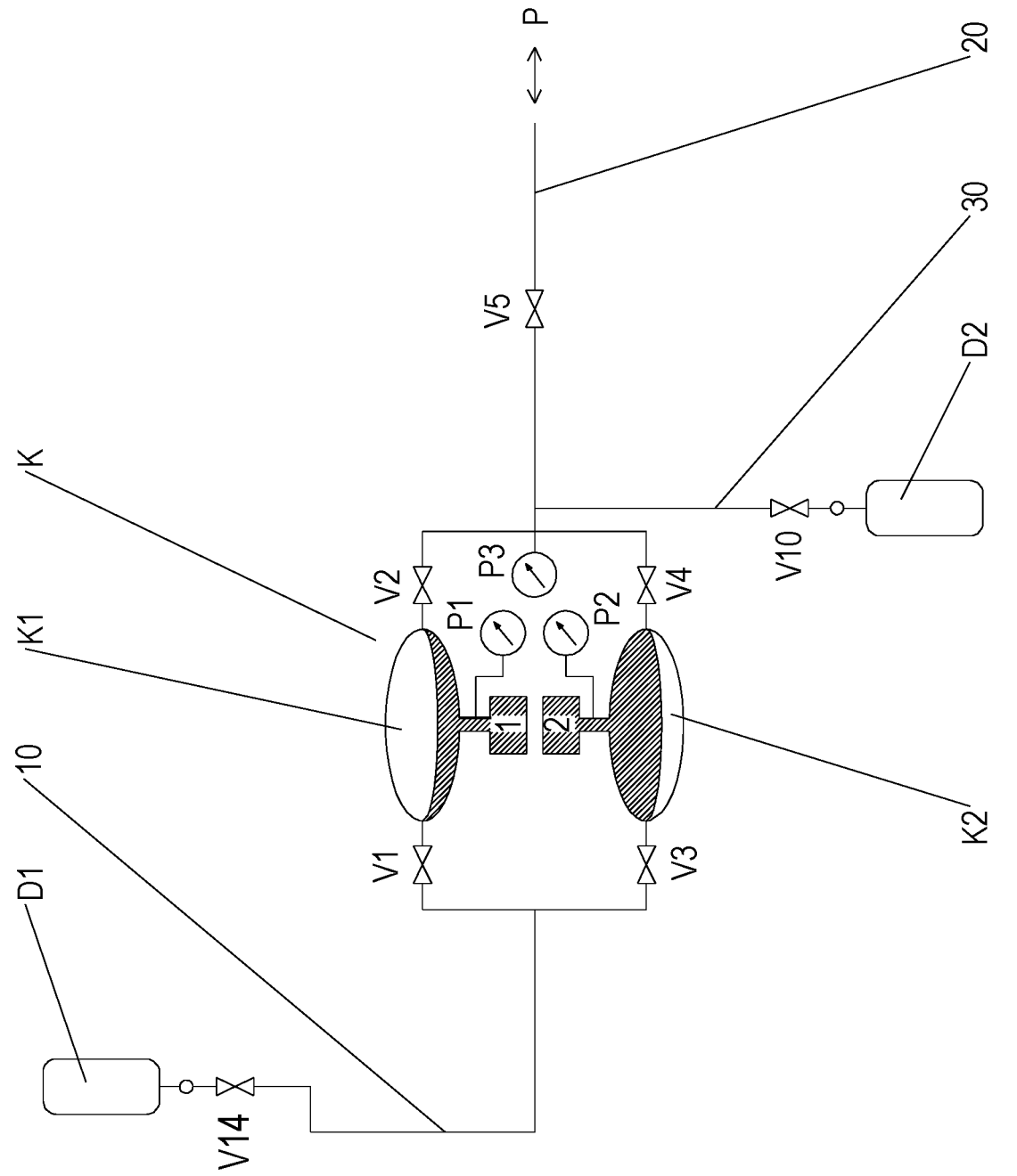

APPARATUS AND METHOD FOR DETERMINING THE STATIC PATIENT PRESSURE

The present invention relates to an apparatus and to a method for determining the static patient pressure.

During a peritoneal dialysis treatment, a volume of dialysis fluid is introduced into the abdomen of a patient via a patient line and is left there for a specific dwell time. The peritoneum acts as a semipermeable membrane that enables a substance transition from the blood into the dialysis fluid during the dwell time of the dialysis fluid in the abdomen, whereby a blood purification is achieved.

After a specific dwell time, the dialysis fluid is completely or partially drained from the abdomen through the patient line and fresh dialysis fluid is introduced into the abdomen.

A vacuum arises during the complete outflow, i.e. during the discharge of the dialysis solution from the abdomen. This pressure measured in the dialysis solution is composed of the dynamic pressure caused by the flow of the dialysis solution, i.e. the conveying pressure caused by the flow resistance, of the static pressure caused by the vertical position of the patient, and of the pressure in the abdomen, i.e. of the peritoneal pressure.

The pressure measured in this manner thus comprises the sum of the individual part pressures so that it is not possible for the dialysis machine or for the user to associate the measured overall pressure with individual pressure components.

To detect the static pressure portion, it is necessary to eliminate dynamic pressure portions, i.e. to stop the pump for conveying the dialysis solution. The static pressure portion lays down how much energy has to be applied by the pump to overcome the vertical difference between the patient and the pump or the dialysis machine.

A procedure is, for example, conceivable in which e.g. at the start of the outflow phase, i.e. at the start of the emptying of the abdomen of the patient, the pump is traveled to a neutral position and is then stopped and the pressure in the pump chamber is adjusted so that no excess pressure is present in the pump chamber. A flow path between the pump and the patient line is subsequently established. The pressure now adopted maps the patient position and represents the static pressure portion. It reflects the vertical difference between the patient and the pump.

This assumption is, however, only correct when the patient line is not partially or completely closed, such as kinked. If, for example, the patient line were closed, the suction pressure of a previous outflow phase would falsify the measured pressure value to the extent that too low a pressure is measured. The dialysis machine would conclude too low a patient position from the low measured static pressure and would accordingly increase the suction pressure on the emptying of the patient to effect the assumed large vertical difference between the patient and the pump. This increase in the suction pressure of the pump can produce a risk for the patient.

In the case of a closure of the patient line, a pressure value is thus admittedly likewise determined, but does not correspond to the static pressure portion that permits conclusions on the vertical position of the patient.

It is known from WO 2016/080883 A1 to conclude a kinked hose by assignment of an increased measurement pressure.

Against this background, it is the underlying object of the present invention to further develop an apparatus of the initially named kind such that a determination of the correct static patient pressure is possible.

This object is achieved by an apparatus for determining the static patient pressure of a peritoneal dialysis patient, wherein the apparatus comprises a patient line, a pump in communication with the patient line for conveying a dialysis solution into the abdomen of the patient, and blocking means, in particular a valve by which the patient line is blockable, characterized in that the apparatus has a pressure chamber that is in fluid communication with the patient line with an open blocking element, with a pressure measurement device furthermore being provided that is arranged such that it measures the pressure in the pressure chamber or a pressure correlated with it; and in that the apparatus comprises a control unit that is configured such that it effects a pressure build-up in the pressure chamber to a measurement pressure in a first step and opens the blocking element in a second step so that the patient line or a part section thereof is acted on by the measurement pressure of the pressure chamber and with the apparatus having an evaluation unit that evaluates the measured pressure after the opening of the blocking element.

The apparatus in accordance with the invention for determining the static patient pressure has a pump that is connected to a patient line for conveying a dialysis solution into the abdomen. The term "patient line" is to be understood as the line, in particular the hose line, that leads from the apparatus to the patient. The term "patient line" can also include the patient catheter, i.e. the line section that is fixedly connected to the patient and that leads into the abdomen of the patient. The term patient line can, however, also be understood as the line section up to the patient catheter.

The apparatus has at least one measurement device for measuring the pressure e.g. in the dialysis solution. This pressure sensor can be arranged at any desired point of the apparatus at which a change of the static pressure of the dialysis solution can be measured. It is arranged such that it measures a pressure or a pressure change that results when the blocking element of the patient line is opened.

A blocking means is furthermore provided, in particular a valve, by which the patient line can be blocked.

The apparatus furthermore has at least one pressure chamber that is in fluid communication with the patient line with an open blocking element and a control unit that is configured such that it effects a pressure build-up in the pressure chamber to a measurement pressure in a first step and opens the blocking element in a second step so that the patient line or a part section thereof is acted on by the measurement pressure of the pressure chamber. The blocking element of the patient line is preferably closed during the pressure build-up.

The pressure sensor is arranged such that it measures the change of the pressure in the pressure chamber or in an element in fluid communication therewith or a pressure correlated therewith.

The evaluation unit of the apparatus detects the measured pressure after the opening of the blocking element and evaluates it.

If the patient line is free, i.e. neither kinked or reduced in its inner diameter nor fully closed, the pressure built up in the pressure chamber can propagate or equalize in the patient line and in the abdomen of the patient. The static patient pressure is adopted that reflects the vertical difference between the patient and the apparatus or the peritoneal dialysis machine. It is possible to measure the static patient pressure in this manner.

If, however, the patient line is closed, the measurement pressure built up in the pressure chamber cannot propagate over the total patient line into the abdomen, which has the consequence that a different measured pressure value is adopted than for the case of a free patient line.

If the patient line is kinked or if it has a reduced flow diameter, the pressure equalization between the pressure chamber and the patient line takes place at a smaller speed than with a free patient line, which can likewise be detected by the evaluation unit.

It is thus possible to draw a conclusion on whether the patient line is closed via the measurement of the pressure and/or the temporal pressure development. If the patient line is completely closed, a pressure value is adopted within a comparatively short time that is higher than the pressure value that would result with a free patient line. If the patient line is reduced in flow cross-section, but not completely closed, the static pressure is optionally adopted, but only after a longer time period than with a free patient line.

The control unit is preferably configured such that the measurement pressure built up in the pressure chamber is larger than the suction pressure in the patient line after the opening of the blocking element.

The pressure chamber is preferably a component of the pump such as the pressure side of a membrane pump. It can, however, also be arranged at a different point, e.g. between the pump and the patient line.

The pressure chamber can be any desired element into which the dialysis solution can be conveyed and can be held pressurized therein until the measurement is carried out. It is conceivable that the pressure chamber is formed by a part of a disposable cassette.

The cassette can have means for controlling the dialyzate flow and/or blocking means for suppressing the dialyzate flow or can cooperate with actuators that effect such a flow control or blocking. The cassette preferably also comprises the pump and/or the pressure chamber.

The evaluation unit can be configured to compare the pressure measured after the opening of the blocking element with a reference pressure. Depending on the measured pressure or on the difference between the measured pressure and the reference pressure, a conclusion can be drawn, on the one hand, on whether the patient line or the abdomen is closed. On the other hand, a conclusion can be drawn from the measured pressure or from the difference of the measured pressure and the reference pressure on the position at which the patient line is clogged or kinked. In a preferred embodiment of the invention, the evaluation unit is configured such that it can carry out one or both tests.

The higher the measured pressure is, i.e. the smaller the difference from the initial measurement pressure in the pressure chamber and the measured pressure is, the closer the closure, etc. of the patient line to the pressure chamber.

In general, the absolute value of the measured pressure, its development over time, or its difference from a reference pressure, or the time development of this difference can be used for the evaluation in the evaluation unit. The reference pressure can be any desired pressure, with the reference pressure also being able to be formed by the measurement pressure that is provided in the pressure chamber prior to the measurement.

If the measured pressure or its difference from a reference pressure or the speed of the pressure change exceeds or falls below a limit value or reaches said limit value, a conclusion can be drawn on a partly or completely blocked patient line depending on the determination of the reference pressure.

The evaluation unit can, for example, be configured to draw a conclusion on a closed or kinked patient line when the difference between the measurement pressure built up in the pressure chamber and the pressure measured after the opening of the blocking element and/or when the speed of the change of the measured pressure does not reach a limit value.

It is conceivable that the evaluation unit is configured such that it sets the suction pressure of the pump in dependence on the measured pressure or on the time development of the measured pressure. If the patient line is kinked or partly clogged, the pump has to provide a higher suction power than with a free patient line, i.e. a neither partly nor completely clogged or kinked patient line.

The evaluation unit is preferably configured such that it outputs a visual or acoustic alarm when the evaluation shows that the patient line is not free.

This can e.g. be determined in that the difference between the measurement pressure built up in the pressure chamber and the pressure measured after the opening of the blocking element and/or the speed of the change of the measured pressure does not reach a limit value.

As stated above, the evaluation unit can be configured such that it carries out a localization on the basis of the measured pressure or its change speed or the respective difference from a reference value or from a reference speed as to at which point a constriction or a closure of the patient line is present.

It can thus not only be determined that the patient line is partly or completely clogged or kinked, but the position at which this is the case can also be localized.

The present invention furthermore relates to a peritoneal dialysis machine comprising at least one apparatus as described herein.

The present invention furthermore relates to a measurement process for determining the static patient pressure, with the method comprising the following steps:
a. Building up a measurement pressure in a pressure chamber while the patient line is separated from the pressure chamber by a blocking means;
b. Opening the blocking means; and
c. Measuring the pressure and/or the time pressure change after the opening of the blocking means; and
d. Evaluating the measured pressure and/or the pressure change in accordance with step c).

It can be determined by the evaluation in accordance with step d) whether the patient line is free, clogged, or reduced in its free flow cross-section.

The method is preferably carried out by means of an apparatus in accordance with the present invention or by means of a peritoneal dialysis machine comprising at least one apparatus in accordance with the present invention.

A conclusion can be drawn on a closed or kinked patient line when the measured pressure or when the difference between the measurement pressure built up in the pressure chamber and the measured pressure and/or when the speed of the change of the measured pressure does not exceed a limit value.

To take account of the changed flow resistance with a suction line that is e.g. partly clogged, the suction pressure of the pump is preferably set in dependence on the measured pressure or on the time development of the measured pressure.

Further details and advantages of the invention will be explained in more detail with reference to an embodiment shown in the drawing.

The only FIGURE shows a schematic flowchart of a peritoneal dialysis machine in accordance with the present invention.

Reference symbol D1 denotes a bag or another container containing fresh dialysis solution. It is in fluid communication with the line 10. The line 10 is blockable by the valve V14 and is in communication with the suction lines of the membrane pumps 1 and 2 via a branch. As can be seen from the FIGURE, blocking valves V1 and V3 are located in the suction lines of the pumps.

Reference symbols P1 and P2 denote pressure sensors that are arranged to measure the respective pressure in the hydraulic medium of the membrane pumps 1 and 2.

Blocking valves V2 and V4 are arranged in the pressure lines of the pumps 1 and 2.

The valves V1 to V4 are preferably controlled so that the pumps 1 and 2 are operated alternately in operation of the machine so that a continuous flow of dialysis solution is achieved.

Reference numeral 20 denotes the patient line in which the blocking valve V5 is located. Fresh dialyzate moves to the patient and consumed dialyzate moves from the patient P to the drainage bag or other drainage container D2 via the patient line 20. The valve V10 is located in the drainage line 30.

The pumps 1, 2 have pressure chambers K1, K2. They can be components of a cassette that can be formed as a disposable. The pressure pick-up or the pressure sensor P3 is located between the pressure chamber K1, K2 and the blocking valve V5.

It is emphasized at this point that the pressure sensor P3 is optional. The invention can generally also only be implemented using the pressure sensor and/or sensors P1 and/or P2.

The pressure measurement could also conversely only take place with the pressure sensor P3 so that the invention is only implemented with this measurement value and not while using the pressure values of the sensors P1 and/or P2.

It is also covered by the invention that the values determined at the hydraulic side (pressure measurement P1/P2) and cumulatively the values determined at the dialyzate side (pressure measurement P3) are used as part of the invention.

Both an alternative and a cumulative arrangement of sensors at the hydraulic side and/or at the dialyzate side or their use as part of the present invention are thus conceivable and covered by the invention within the framework of the present invention.

An increased positive pressure is built up by means of the pumps 1 or 2 or by means of both pumps 1, 2 in the pressure chamber K1, K2 before the calibration of the static patient pressure. The valve V5 is closed here. After the build-up of the pressure (measurement pressure) in the pressure chamber K1, K2, the valve V5 in the patient line is opened and the pressure and/or its time development is/are measured by means of the pressure sensor P3.

If the patient line 20 is free, the built-up measurement pressure in the patient line 20 and in the abdomen of the patient P equalizes. The static patient pressure is adopted that reflects the vertical difference of the patient from the dialysis machine.

If the patient line 20 is, however, not free, but rather closed, a pressure change is optionally admittedly also measured, but it is a falsified measurement value here that would have the result that too high a patient position is determined because the measurement pressure only drops—if at all—by a relatively small amount. The energy amount of the pump is reduced.

This behavior causes the suction pressure to increase with a closed patient line and results in a more gentle start-up behavior.

Said positive measurement pressure in the chamber K1, K2 should be selected such that the applied suction pressure is superposed. In this respect, the volume relationships of the hose set to the patient line and the applied suction pressure have to be taken into account.

One or both of the pumps shown can be used to build up the measurement pressure.

If the patient is still filled with dialysis solution when the method is carried out, no volume displacement takes place to carry out the measurement method in accordance with the invention. A separate patient line check is no longer necessary since the system corrects itself. The invention is, however, generally also usable in a condition in which the patient is partly or completely emptied.

A preferred procedure of the method is as follows:

The peritoneal dialysis machine is at the start or before a start-up phase, i.e. before the emptying of the patient.

The hydraulic pumps 1, 2 are operated into a pump region which allows an excess pressure to be built up in the chamber K1 and/or K2 without being exposed to the influence range of the pump membrane.

The pressure in the total cassette K is raised into an excess pressure range, e.g. to a pressure value in the range from 50 mbar to 400 mbar, preferably in the range from 200 mbar to 300 mbar, and, for example, to a pressure value of 250 mbar.

A flow path between the cassette K and the patient line 20 is established by opening the valve V5 and the pressure is measured.

This can take place via the pressure sensors P1 or P2 arranged at the hydraulic side or also by a pressure measurement in the dialysis solution, for example by means of the pressure sensor P3. As stated above, the pressure measurement can take place alternatively or cumulatively by means of the pressure sensors at the hydraulic side or by means of the pressure sensors at the dialyzate side.

The pressure now adopted maps the patient position i.e. represents the static patient pressure.

The value determined is supplied to an evaluation unit, not shown.

The valve V10 of the line 30 and the suction valves V1 and V3 are closed during the method.

If the patient line 20 is free, the pressure in the chambers K1, K2 will propagate via the patient line 20 with open valves V2, V4, and V5 into the abdomen of the patient. The pressure at the sensors P1, P2, P3 drops.

If the patient line 20 is not free, but clogged, the pressure with open valves V2, V4 and V5 in the chambers K2, K2 will only propagate into the patient line 20 up to the kink point or to the point of the clogging. The pressure at the sensors P1, P2, P3 likewise drops, but only by a smaller amount than with a free patient line.

If the patient line is not completely clogged or kinked, but only the free flow cross-section, a slowed down pressure reduction occurs with respect to a free patient line.

The evaluation unit detects the pressure value after the opening of the valve V5 or the pressure development after the opening of the valve. A calculation algorithm of the evaluation unit determines whether the patient line is partly or completely blocked or clogged and if so, where this is the case.

Based on the evaluation of the evaluation unit, the power of the pumps can be correspondingly adapted because a partly clogged patient line has a larger flow resistance than a free patient line and thus a greater suction power.

If the patient line is partly or completely clogged, an alarm can be output that makes the user aware of it.

The invention claimed is:

1. A peritoneal dialysis machine comprising at least one apparatus for determining static patient pressure of a peritoneal dialysis patient, wherein the apparatus comprises:
    a patient line,
    a pump in communication with the patient line for conveying a dialysis solution into an abdomen of the patient,
    a valve by which the patient line is blockable,
    a pressure chamber that is in fluid communication with the patient line via an open blocking element,
    a pressure measurement device that is arranged such that it measures a pressure in the pressure chamber or a pressure correlated with the pressure in the pressure chamber,
    a control unit that is configured such that it effects a pressure build-up in the pressure chamber to a measurement pressure in a first step and opens the blocking element in a second step so that the patient line or a section thereof is acted on by the measurement pressure of the pressure chamber, and
    an evaluation unit that evaluates a measured pressure after the opening of the blocking element and is configured such that it carries out a localization as to a position at which a constriction or a closure of the patient line is present based on a change between the measurement pressure and the measured pressure after the opening of the blocking element and/or based on a speed of the change between the measurement pressure and the measured pressure.

2. A peritoneal dialysis machine in accordance with claim 1, characterized in that the control unit is configured such that the measurement pressure is larger than a suction pressure in the patient line after the opening of the blocking element.

3. A peritoneal dialysis machine in accordance with claim 1, characterized in that the pressure chamber is arranged between the pump and the patient line or in that the pressure chamber forms a component of the pump.

4. A peritoneal dialysis machine in accordance with claim 1, characterized in that the pressure chamber is formed by a part of a disposable cassette.

5. A peritoneal dialysis machine in accordance with claim 4, characterized in that the disposable cassette comprises the pump and/or the pressure chamber and/or means for controlling a flow of the dialysis solution and/or blocking means for suppressing a flow of the dialysis solution.

6. A peritoneal dialysis machine in accordance with claim 1, characterized in that the evaluation unit is configured to draw a conclusion of a degree of closure on a partly or completely closed patient line when the change between the measurement pressure and the measured pressure after the opening of the blocking element does not exceed a limit value and/or when the speed of the change between the measurement pressure and the measured pressure does not exceed a limit value.

7. A peritoneal dialysis machine in accordance with claim 1, characterized in that the evaluation unit is configured such that it sets a suction pressure of the pump based on the measured pressure or on a time development of the measured pressure.

8. A peritoneal dialysis machine in accordance with claim 1, characterized in that the evaluation unit is configured such that it outputs an alarm when it is found that the patient line is not free from being partly or completely clogged or kinked.

* * * * *